(12) United States Patent
Zarling et al.

(10) Patent No.: US 10,828,163 B2
(45) Date of Patent: Nov. 10, 2020

(54) PROSTHESIS SYSTEM

(71) Applicants: Sven Zarling, Duderstadt (DE); Dieter Föllmer, Erfurt (DE)

(72) Inventors: Sven Zarling, Duderstadt (DE); Dieter Föllmer, Erfurt (DE)

( * ) Notice: Subject to any disclaimer, the term of this patent is extended or adjusted under 35 U.S.C. 154(b) by 251 days.

(21) Appl. No.: 15/522,351

(22) PCT Filed: Oct. 15, 2015

(86) PCT No.: PCT/DE2015/100428
§ 371 (c)(1),
(2) Date: Apr. 27, 2017

(87) PCT Pub. No.: WO2016/066158
PCT Pub. Date: May 6, 2015

(65) Prior Publication Data
US 2017/0348106 A1    Dec. 7, 2017

(30) Foreign Application Priority Data
Oct. 28, 2014    (DE) .......................... 10 2014 115 676

(51) Int. Cl.
*A61F 2/30*    (2006.01)
*A61F 2/78*    (2006.01)
(Continued)

(52) U.S. Cl.
CPC ........ *A61F 2/30749* (2013.01); *A61F 2/2814* (2013.01); *A61F 2/38* (2013.01);
(Continued)

(58) Field of Classification Search
CPC ........ A61F 2/2814; A61F 2/38; A61F 2/4202; A61F 2/7812; A61F 2002/30649; A61F 2002/7887
See application file for complete search history.

(56) References Cited

U.S. PATENT DOCUMENTS

| | | | |
|---|---|---|---|
| 6,454,808 B1 * | 9/2002 | Masada ................. | A61F 2/4241 623/21.15 |
| 7,922,773 B1 | 4/2011 | Kuiken | |
| 9,730,797 B2 * | 8/2017 | Gonzalez-Hernandez ................. | A61F 2/4612 |

(Continued)

FOREIGN PATENT DOCUMENTS

| | | |
|---|---|---|
| DE | 19932388 C1 | 12/2000 |
| GB | 2468967 A | 9/2010 |

(Continued)

OTHER PUBLICATIONS

Blunn, Unwin. Derwent abstract of GB2468967A. (Year: 2010).*
Louka, Maria, "International Search Report," prepared for PCT/DE2015/100428, dated Feb. 9, 2016, four pages.

*Primary Examiner* — Christie L Bahena
(74) *Attorney, Agent, or Firm* — Shackelford, Bowen, McKinley & Norton, LLP (57) ABSTRACT

In the case of known prosthesis systems and socket supplies, the transmission of force is a critical issue. The inventive prosthesis system shall improve known prosthesis systems. According to the invention, a prosthesis system for human limbs is provided, which comprises an implant (101) having at least two joint parts which are movable relative to each other, wherein the first joint part (110) can be connected to a bone part (131, 132) and the second joint part (120) comprises a subcutaneously arrangeable end part (124) on the side being remote from the joint. The invention further relates to a prosthesis system comprising a subcutaneous implant and a socket (170).

15 Claims, 9 Drawing Sheets

(51) Int. Cl.
*A61F 2/28* (2006.01)
*A61F 2/38* (2006.01)
*A61F 2/80* (2006.01)

(52) U.S. Cl.
CPC .............. *A61F 2/78* (2013.01); *A61F 2/7812* (2013.01); *A61F 2/80* (2013.01); *A61F 2002/30649* (2013.01); *A61F 2002/7887* (2013.01)

(56) References Cited

U.S. PATENT DOCUMENTS

| | | | | |
|---|---|---|---|---|
| 9,855,153 | B2 * | 1/2018 | Unwin | A61F 2/389 |
| 2007/0150070 | A1 | 6/2007 | Kim et al. | |
| 2007/0185584 | A1 * | 8/2007 | Kaufmann | A61F 2/4241 |
| | | | | 623/21.15 |
| 2008/0161938 | A1 * | 7/2008 | Gramnas | A61F 2/60 |
| | | | | 623/33 |
| 2011/0098603 | A1 * | 4/2011 | Deirmengian | A61F 2/4657 |
| | | | | 600/587 |
| 2014/0303539 | A1 * | 10/2014 | Baym | A61B 5/0031 |
| | | | | 602/23 |
| 2014/0303741 | A1 * | 10/2014 | Macduff | A61F 2/4241 |
| | | | | 623/21.15 |
| 2015/0351940 | A1 * | 12/2015 | Lacraz | A61F 2/78 |
| | | | | 623/16.11 |

FOREIGN PATENT DOCUMENTS

| | | |
|---|---|---|
| WO | WO-03065938 A1 | 8/2003 |
| WO | WO-2007001223 A1 | 1/2007 |
| WO | WO-2010070614 A1 | 6/2010 |

\* cited by examiner

PROSTHESIS SYSTEM

The invention relates to a prosthesis system for human limbs having an implant having at least two joint members which can be moved relative to each other, wherein both joint members are configured to be arranged intracorporeally. The invention further relates to a prosthesis system comprising a subcutaneous implant and a shaft.

TECHNOLOGICAL BACKGROUND

Prosthesis systems for human limbs after amputation or exarticulation have been known for some time. These prostheses can be used as intracorporeal implants which can be connected to a bone portion and which are surrounded by bodily tissue. These endoprostheses or implants are suitable for the long-term use of a patient and can be connected, after the limb stump has healed, to limb prostheses, so-called exoprostheses, fitted outside the human body. Examples of artificial joints after an amputation at the upper leg are knee joint, lower leg and foot prostheses. In the case of amputations or exarticulations in the region of the upper end, upper arm and/or lower arm prostheses are required.

Generally, the patients receive so-called shaft prostheses, wherein the shaft surrounds the stump on all sides and is used to transmit the force of the stump to at least one artificial member of an exoprosthesis. A critical point for the function of a prosthesis is the force transmission. In a shaft for leg prostheses, different forces act, such as impact, rotation and shearing forces. In particular during running, there is the problem that there occurs during the force transmission from the shaft to the soft part mantle forces which may lead to swellings, pressure sores and inflammations on the leg stump.

STATEMENT OF INVENTION

On the basis of the present invention, the above-mentioned disadvantages of known shaft fittings are intended to be reduced and a more rapid care of amputee patients is intended to be ensured by locating an accurately fitting shaft more rapidly. In this instance, the force transmission from a shaft to the prosthesis system is intended to be optimised.

Furthermore, the formation of the remaining musculature in the stump is not intended to be restricted as in conventional prosthesis systems. Another object of the present invention is to allow use of the muscles for controlling prosthesis components.

Another object of the present invention is to improve the wearing comfort of a shaft prosthesis system.

Against this background, an object of the present invention is to provide an improved prosthesis system.

The object is achieved by a prosthesis system comprising an implant which is intended to be arranged subcutaneously and which has the features of claim 1. The dependent claims relate to advantageous developments.

A prosthesis system for human limbs is provided according to the invention and has an implant having at least two mutually movable joint members, wherein the first joint member can be connected to a bone portion and the second joint member has an end portion which is intended to be arranged subcutaneously at the side thereof remote from the joint.

As a result of the provision of an articulated end portion of the implant, the intracorporeal end portion can better take up loads or forces from the stump. Forces which have to be controlled result in particular during use of a connected extracorporeal prosthesis. The two joint members form a movable connection, wherein suitable one-axis, two-axis or three-axis articulation types, such as, for example, film hinges, ellipsoid joints or ball-and-socket joints can be used.

If the implant is connected, for example, to an upper leg bone, the natural inclination of the upper leg bone can advantageously be compensated for by the movability of the second joint member.

Forces which act on the stump end in the case of arm amputees can also be better received by an articulated end portion of the implant. For example, axial and non-axial forces which occur as a result of the weight of a lower arm prosthesis or in the case of press-ups can better be transmitted into the arm stump.

According to an advantageous development of the prosthesis system, the end portion of the second joint member is constructed in a plate-like manner.

The plate-like end portion or the end plate can be integrally connected to the second joint member or can be fixed with suitable fixing means to the second joint member. The end plate can, for example, be screwed on. In this case, the form of the end plate may be selected so that the end plate can be adapted to the size of the stump end.

The loading face can thereby be increased and occurring forces can be advantageously distributed over the surface-area. This is in contrast to a relatively small cut face of a bone stump which can only take up forces in a point-like manner. Such point loads cause pain and where applicable tissue damage. Therefore, the bodyweight was conventionally taken up on the tuber with increased structural complexity.

Complex constructions for displacing the load receiving face into the tuber region and point loads and damage connected therewith in respect of the soft part mass can be prevented by means of the movably supported end plate. The load-bearing capacity of the amputation stump is significantly improved by providing a preferably edge-free end portion of the second joint member because pressure sores and injuries to the soft parts can be reduced.

As a result of the defined end portion of the second joint member, the position of the distal end of the bone is readily able to be located. In conventional prostheses, however, the position of the bone shaft end in the soft part region cannot always be readily located and can where applicable involve the risk that soft part tissue may be drilled through.

In the case of a predetermined end plate form, an individual shaping of the limb stumps is advantageously no longer necessary so that rapid patient care can be brought about with a counter-piece which fits the end portion in a shaft. The termination of the stump with a predetermined outer form of the movable end portion allows time-related possible changes of the soft part tissue in the distal stump region to be disregarded. It is thereby advantageously possible to dispense with complex reprocessing operations or re-adaptations of the shaft after being worn for specific lengths of time.

A development of the invention makes provision for an anatomically adapted contact face to be formed at the outer side of the second joint member. The anatomically adapted contact face makes it possible for the skin to be able to slide over the surface in a manner which is as natural as possible. The face supports a precisely fitting integration of the prosthesis with a counter-piece of the shaft. Injuries and pressure sores are prevented by means of the anatomically adapted contact face without sharp edges and the intracorporeal prosthesis can be prevented from slipping with respect to the shaft or the extracorporeal prosthesis which can be connected thereto in conjunction with a correspondingly formed counter-piece of a shaft.

In a preferred development of the prosthesis system, the end portion has a convex-curved outer face.

In this manner, a uniform force transmission can be produced between the end portion and a preferably concave counter-piece in a shaft, whereby pressure sores on the body are prevented.

The convex-curved outer face has the additional advantage that the skin can adjoin it in a slidingly movable manner. In other words, after a subcutaneous arrangement of the implant, the skin can readily slide over the outer face of the end portion of preferably smooth form.

In a preferred development of the prosthesis system, the first joint member can be connected to a bone portion via a medullary pin and/or a screw unit.

With a medullary pin and/or a screw unit, the first joint member can be introduced into the bone channel of a sectioned bone shaft and can consequently be connected. The connection or anchoring is carried out by means of either bone cement or other suitable fixing means. Furthermore, anchoring without fixing means is also conceivable.

The limb stump can be brought to the optimum length by means of a medullary pin. In this manner, for example, a difference in leg length or difference in upper leg length in comparison with the normal leg or upper leg length can be compensated for. By means of a medullary pin, the length of the stump can be varied and can be adapted to the soft tissue situation. If a soft part overhang exists after an amputation, the medullary pin can bridge it.

In a preferred development of the prosthesis system, the first joint member is in the form of an articular head and the second joint member is in the form of an articular socket.

The use of a ball-and-socket joint has the advantage of freedom of movement of three degrees of freedom. Thus, a three-axis ball-and-socket joint is more movable than a single-axis hinge. In this manner, the movable joint member can react optimally to force actions from different directions.

The ball-and-socket joint may have a concave smaller joint face which has contact with a convex larger joint face. In this case, the articular socket can be constructed so as to have an annular projection with resilient means so that the joint ball cannot jump out of the articular socket without application of force. In this manner, the first and second joint members can form a coupled unit whose joint members can be held together independently of muscle connections or position. Known plug type or snap-fit mechanisms or the like can be used for such fixing of the joint members relative to each other, wherein these fixing mechanisms are intended not to limit the sliding of the joint members relative to each other to the greatest possible extent.

In a preferred development of the prosthesis system, the first joint member is constructed in a hollow manner and has fixing means which are selected from the group consisting of bone-forming material, bone cement and adhesive.

If the first joint member is a ball-like articular head, the spherical shell of the articular head can be fitted over the distal shaft end. In this case, suitable fixing means in the spherical shell allow the first joint member to fuse or bond to the bone shaft.

In a preferred development of the prosthesis system, the end portion has a radially peripheral edge region.

By means of the radially peripheral edge region, the outer support face formed is increased. In this case, the outer periphery of the preferably hemispherical end plate can be at least one and a half times the outer diameter of the distal end of the bone shaft. The increased support face reduces the pressure loading by means of a shaft which surrounds the limb stump on tendons and muscles still present. A permanent compression of the soft parts and in particular the musculature can be prevented by the provision of an edge region. The musculature can be formed in an optimum manner as it would in the corresponding healthy limbs.

Advantageously, muscles and/or tendons can be connected in the radial edge region. As a result, the effective strength of the remaining musculature present can be at least partially maintained. The muscles are not unnaturally redirected by the arrangement of an end plate with a radial edge region, as would be the case in a prosthesis without a projecting end plate.

The outer face of the end portion is greater than the outer periphery of the first joint member by means of the radial edge region so that forces can be better introduced and distributed.

In a preferred development of the prosthesis system, the end portion of the second joint member has faces and/or material for connecting muscles.

As a result of securely connecting muscles which can be used for the extension or bending of the amputated limbs, at least a portion of the remaining musculature can be functionally used. The muscles can grow at suitably formed faces, such as, for example, fine-pored anchoring faces. Alternatively or additionally, the inward growth of muscle tissue can be facilitated by the second joint member being coated with a tissue or with lattices of metal or other suitable materials. After the muscle tissue has successfully grown on or fused, the muscular function and stability of the connected muscles can be reproduced. The connection of the present musculature allows movement of the articular end portion or the end plate. As a result of the second joint member which can be deliberately controlled by muscles, an additional extracorporeal prosthesis such as a knee or foot prosthesis can be controlled.

By the muscle volume being maintained, the bone stump can be prevented from floating in the soft part mantle or the entire stump can be prevented from floating in the prosthesis shaft. This ensures greater reliability and greater wearing comfort for the user of the prosthesis system.

In a preferred development of the prosthesis system, the prosthesis system comprises a shaft which at least partially surrounds the limb stump in order to be connected to extracorporeal prosthesis mechanisms.

Advantageously, the shaft has a counter-plate, the form of which is adapted to the outer form of the second joint member.

The predetermined form of the end plate in conjunction with the fitting counter-plate in the shaft has the advantage that an individual form adaptation of the shaft is no longer necessary. In this manner, precisely fitting, industrially produced shaft counter-pieces can be used and can make it easier to care for the patient. A short time after the stump has healed, the shaft can be adapted. The adaptation can be carried out in an optimum manner within a time of a few hours. This time saving can reduce the costs in comparison with prostheses which have to be adapted in a lengthy and repeated manner. Another advantage of the prosthesis system is that the entire course of treatment, including a stay in hospital and rehabilitation stay, can be reduced in terms of time.

As a result of the counter-plate in the shaft being adapted in terms of form to the outer form of the subcutaneous end plate, the main force transmission can be produced here so that the upper shaft edge in the tuber region is no longer required or is required only partially as a support. In a preferred development of the prosthesis system, therefore, the shaft can be constructed as a partially open frame shaft.

The open construction of the shaft instead of a closed container construction allows a better exchange of air and temperature with the environment. As a result, perspiration formation is generally avoided. This improves the wearing comfort for the user. Furthermore, pressure sores can be prevented.

In a preferred development of the prosthesis system, the shaft may have a band extending in a circular manner as a retention device for the shaft.

The circular band forms a bandage whose periphery can be adjusted in a variable manner in accordance with the stump periphery. This allows good retention of the shaft. The shaft is also suitable for use in water as a result of the adjustable band acting as a retention device for a shaft.

In order to fix the band to the shaft, the outer side of the band has retention means which can cooperate with corresponding retention means of the shaft in a positive-locking manner.

Furthermore, the band may have measurement sensors for myosignals. Myosignal sensors can be arranged in the band on the side facing the skin or alternatively on the free skin surface in order to detect the contraction of the bending or stretching muscles. Myoelectrical signals can be measured, for example, via electrodes on the skin. In this instance, myoelectrical signals are electrically measurable signals which result during the conscious and unconscious contraction of muscles. The measurement of the muscle movements can be used advantageously for controlling the prosthesis system in order to control movements of the exoprosthesis, such as, for example, knee bends or gripping movements in the case of the hand.

In a preferred development of the prosthesis system, there is provided at least one external measurement system which has measurement sensors for detecting the position of the second joint member. In this case, the at least one external measurement system can preferably be formed under the stump as a counter-plate and/or as a pipe element.

It is thereby possible to dispense with measurement sensors on the skin or in the band. For example, it is simply necessary to detect the position of the second joint member by means of the measurement sensors in the counter-plate. As a result, the movement of the end plate by muscles can be indirectly measured. If electrical cable connections are used for receiving and forwarding the detected measurement signals, they can be integrated in the shaft construction.

Alternatively or additionally to an external measurement system, at least one internal measurement system can be provided. For internal measurements in the implant, for example, the second joint member has measurement sensors in order to detect the position of the second joint member. These measurement sensors can transmit the data detected to a control unit wirelessly. A sensor unit integrated in the end plate can ensure the functionality of the extracorporeal prosthesis. The measurement sensors in the implant can also be provided in addition to one or more sensors in the counter-plate in order to be able to use signals for control and/or loading measurements of the intracorporeal components.

In a preferred development of the prosthesis system, the prosthesis system has a control unit, wherein extracorporeal prosthesis mechanisms can be controlled or regulated on the basis of the measurement signals detected.

On the basis of the position data of the joint plate detected by these measurement sensors (for example, status when inclined forwards or inclined backwards), a connected exoprosthesis can be controlled.

The inclination movements mentioned can be controlled by the user himself after the installation of the prosthesis and connection of the muscles to the end portion. As a result of the direct or indirect measurement of the position of the subcutaneously arranged second joint member, the intended movements of the user can readily be forwarded to the extracorporeal prosthesis.

The invention not only provides an optimally positioned, highly loadable prosthesis system but at the same time also affords the possibility of being able to control the extracorporeal prosthesis well. In this instance, an object is to continue to use the natural muscles to the greatest possible extent, where present, or to make them usable via an external trigger.

The movability and independence of the affected person are increased by better functionality of the prosthesis system.

BRIEF DESCRIPTION OF THE FIGURES

Additional advantages and features of the invention will be appreciated from the following description of embodiments with reference to the Figures. In the drawings.

DETAILED DESCRIPTION OF THE FIGURES

The illustrations are schematic and are not necessarily true to scale. Furthermore, they do not show all details but are instead limited to the depiction of the inventively significant details and additional features which make it easier to explain and describe the invention. The same elements in the different Figures are indicated with the same reference numerals.

Embodiments of the invention are explained in greater detail below with reference to the drawings.

Figure 1:
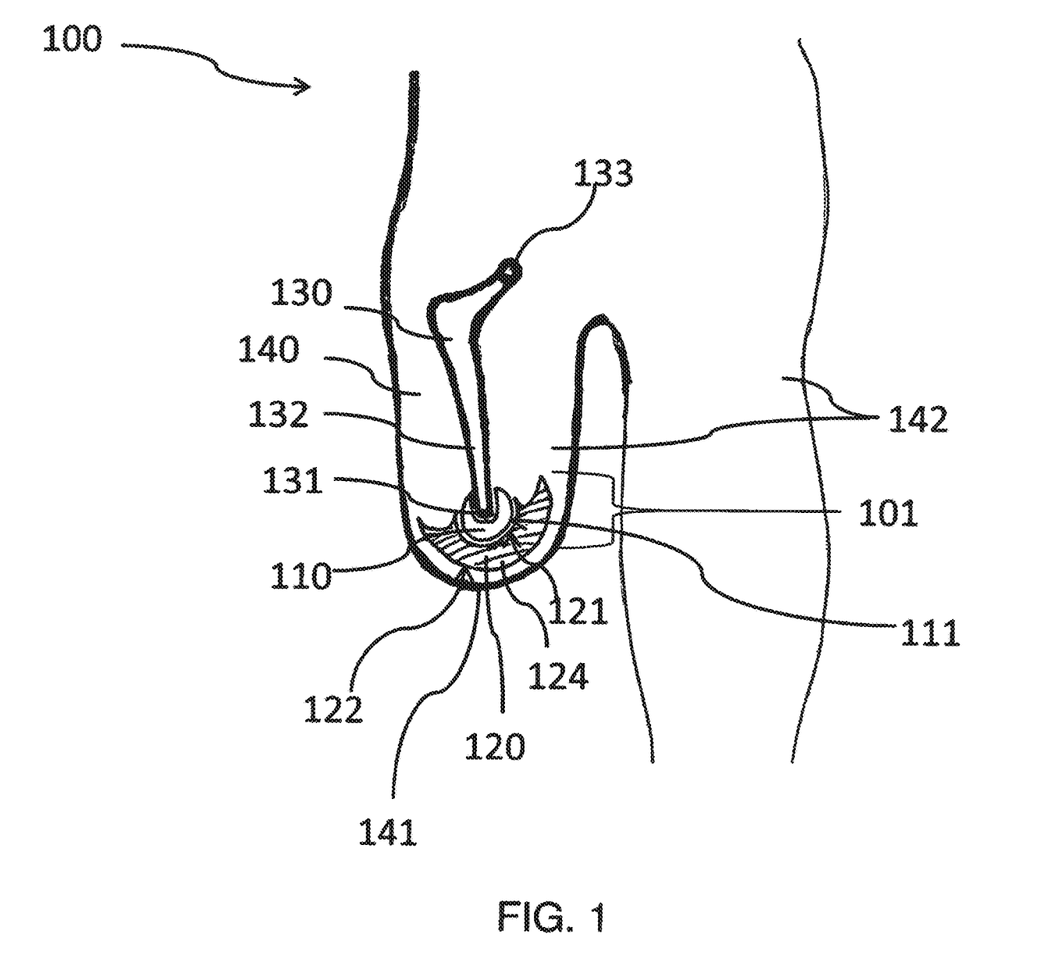
FIG. 1 is a cross-section of a prosthesis system for an upper leg.

FIG. 1 shows a prosthesis system 100 in the form of an upper leg prosthesis. The upper leg 142 has an amputated femur bone 130. The sectioned surface of the bone shaft 132 is located at the distal shaft end 131. The femur head 133 is supported in the hip socket which is not shown. The femur bone 130 is surrounded by a soft part mantle 140.

The implant 101 is arranged exclusively intracorporeally, wherein the first joint member 110 is connected to the distal shaft end 131 with bone cement or in a cement-free manner. The first joint member 110 is constructed as an articular head with a convex sliding face 111. The sliding face 111 of the articular head is in contact with the sliding face 121 of the second joint member 120. The second joint member 120 can be moved around the articular head of the first joint member 110 so that the second joint member 120 can take up different positions.

At the side remote from the joint, the second joint member has an outer face 122 which is arranged subcutaneously. The outer face 122 is convex-curved and can take up pressure or weight forces. The skin can readily slide over the end portion as a result of the curvature.

The second joint member 120 has an integral end portion 124. The implant components can be constructed from different suitable implant materials. In this case, the materials may be rigid and/or flexible. A flexible construction of the radial edge region of the end portion 124 can damp impacts which occur in this region. Furthermore, the entire end portion 124 can be constructed as a shock absorber in order to be able to damp impacts which occur at the distal amputation stump end 141.

Figure 2:
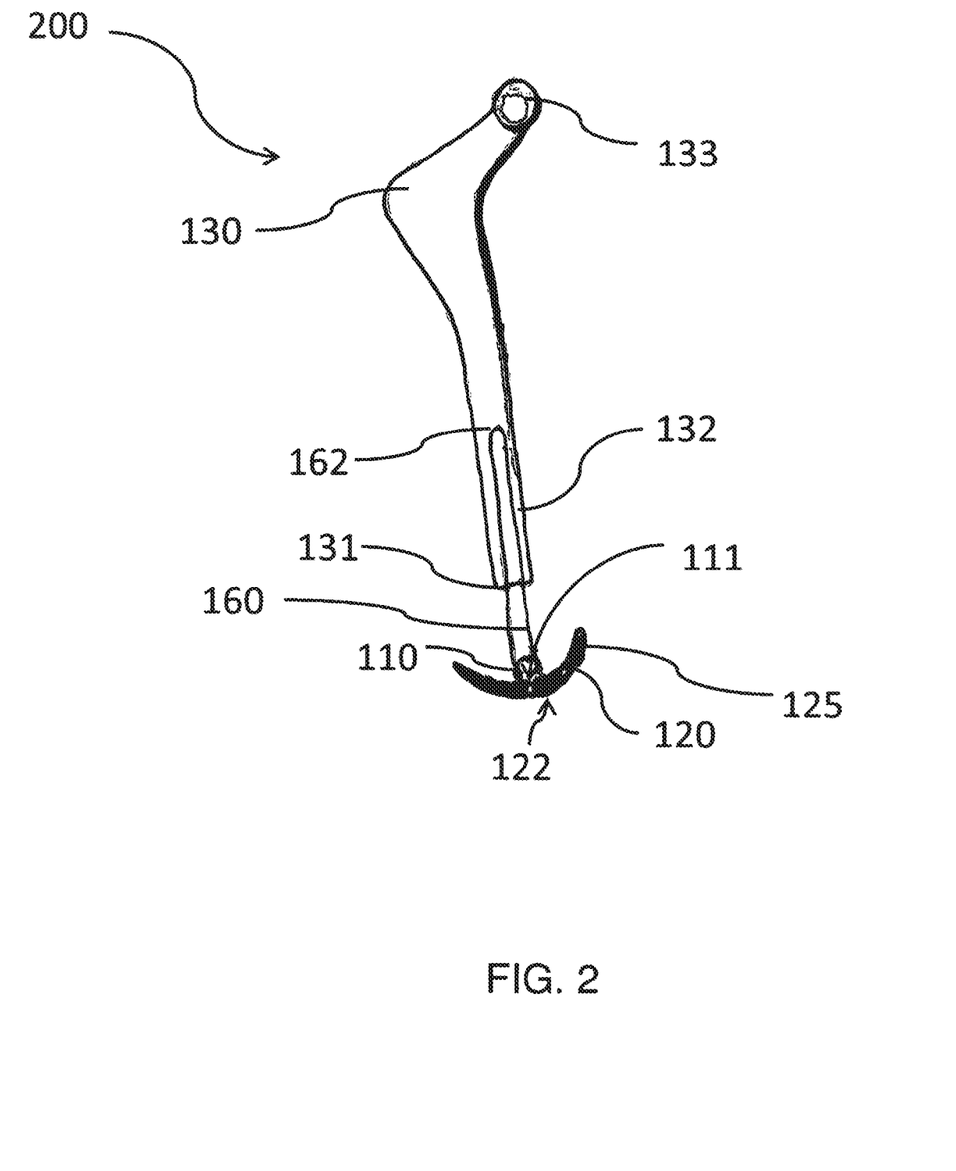
FIG. 2 shows another embodiment of a femur prosthesis system comprising a medullary pin.

FIG. 2 shows another embodiment of a femur prosthesis system 200, wherein the first joint member 110 is anchored via a medullary pin 160 with respect to the femur bone 130. In this instance, the medullary pin 160 is introduced into the bone channel of the sectioned bone shaft 132. The connection with respect to the bone can be produced in a cement-free manner or with suitable fixing means.

The joint of the implant has a spherical sliding face 111, about which the second joint member 120 can move with three degrees of freedom. In other words, the second joint member 120 can be freely moved on the articular head of the first joint member 110. The movement is not limited until the radially peripheral edge region strikes the medullary pin 160. This movability can be further limited depending on the extent of the soft part tissue (not shown in FIG. 2).

Figure 3:
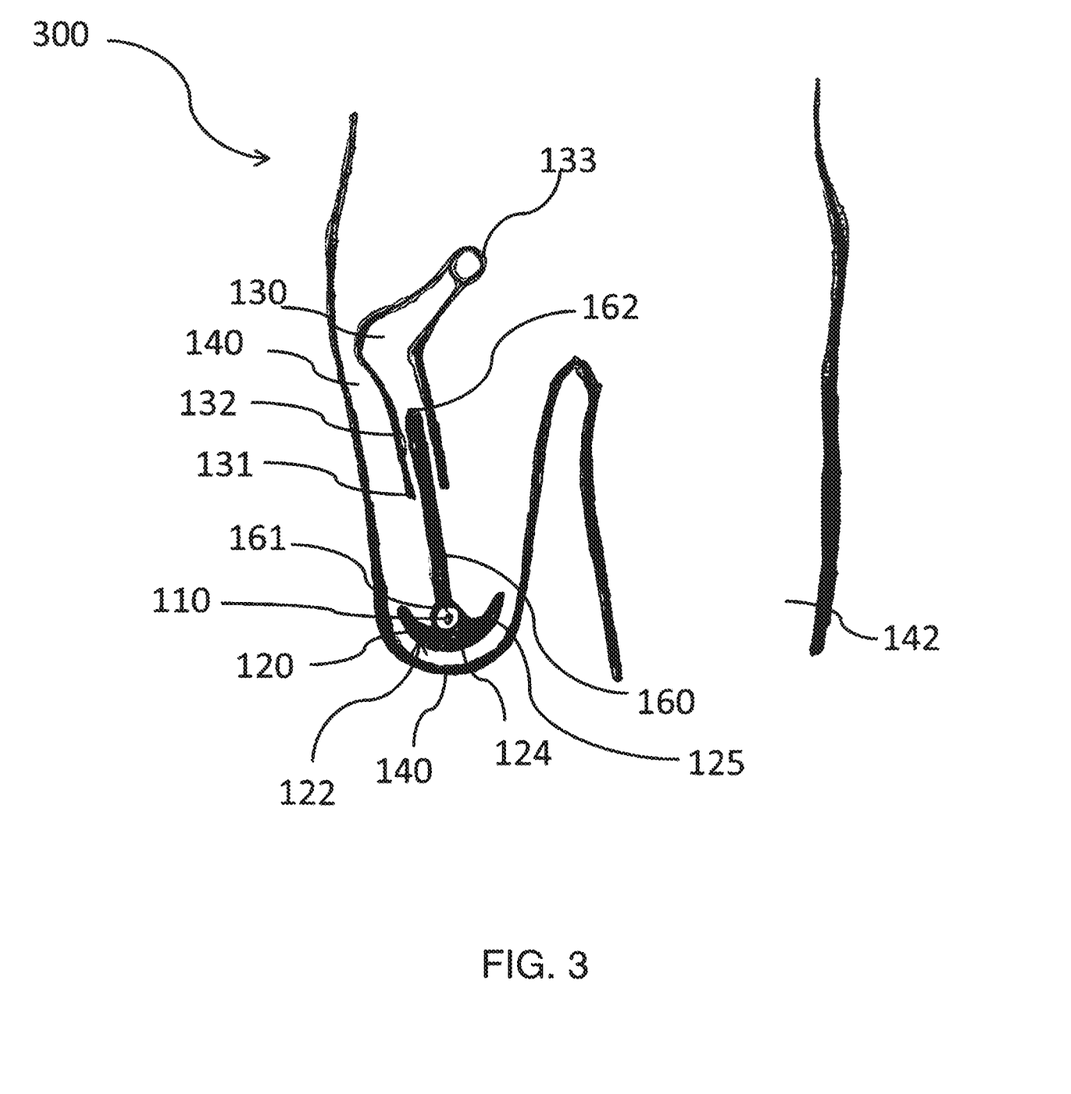
FIG. 3 shows another embodiment of a femur prosthesis system comprising a medullary pin.

FIG. 3 shows a femur prosthesis system 300 with a medullary pin 160, the proximal medullary pin end 162 of which has been inserted in an upper leg 142 of a patient. The proximal medullary pin end 162 can be introduced in a natural femur bone 130. The bone shaft 132 can be connected at the proximal side 132 thereof to a hip endoprosthesis (not shown). The still-intact bone shaft 132 may have a natural connection of the muscles so that movements, for example of the hips, can still be carried out.

The distal medullary pin end 161 is securely connected to the first joint member 110. Muscles still present for extending and bending the leg can be connected to the second joint member 120 at a plurality of locations in order to be able to produce inclination movements of the end portion 124.

If the end portion 124 which is located substantially perpendicularly to the medullary pin is loaded with weight after an exoprosthesis (not shown) has been connected, the second joint member 120 can tilt so that the end portion takes up a substantially horizontal position and consequently compensates for the natural oblique position of the femur bone shaft 132. However, a rigid end plate would produce pressure in the event of loading at the lowest point so that undesirable pressure sores can occur as a result of the point-like loading. If the end portion 124 is orientated substantially horizontally, the forces can be taken up by the joint member 120 in a planar manner. Since the load is distributed over the entire outer face 122, pressure sores can effectively be prevented.

Figure 4:
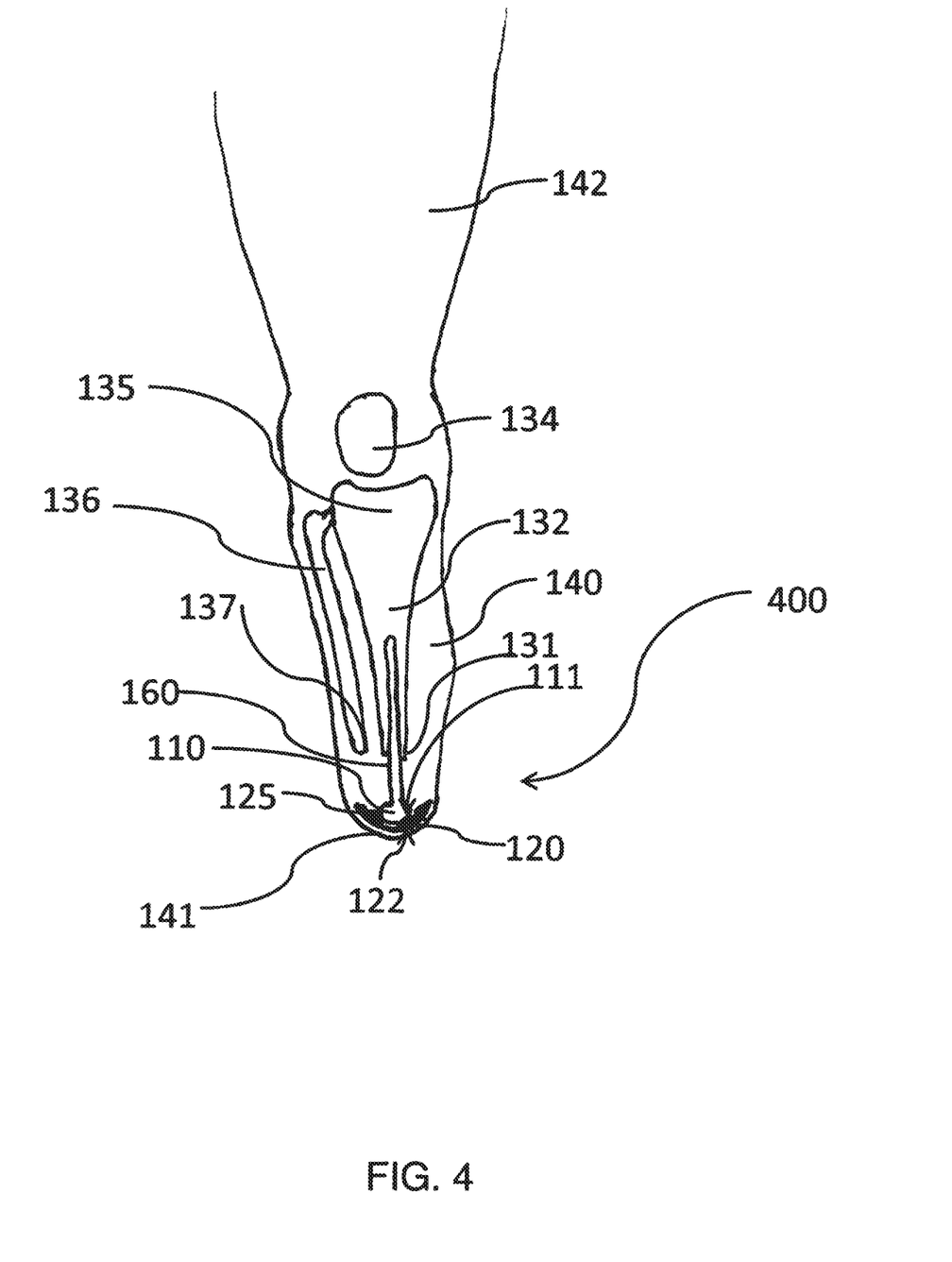
FIG. 4 shows another embodiment of the prosthesis system for a lower leg.

FIG. 4 shows a prosthesis system 400 for a lower leg. There are schematically shown under the upper leg 142 a knee-cap 134 and adjoining low leg bones, the tibia 135 and fibula 136. The distal tibia shaft end 131 is connected to a medullary pin 160. The medullary pin can in this case be fitted in or on the distal end of the tibia because the loading is primarily transmitted via the stronger tibia bone. In the embodiment shown, the distal fibula shaft end 137 is not directly connected to the prosthesis system. The radially peripheral edge region 125 is configured in such a manner that the edge of the second joint member 120 projects beyond the fibula 136. Depending on the length of the fibula bone, the end plate may alternatively to the embodiment shown also be smaller and may not extend beyond the end of the fibula. Both an inclination and a rotation of the end plate can also be brought about here as a result of the musculature being connected.

Figure 5:
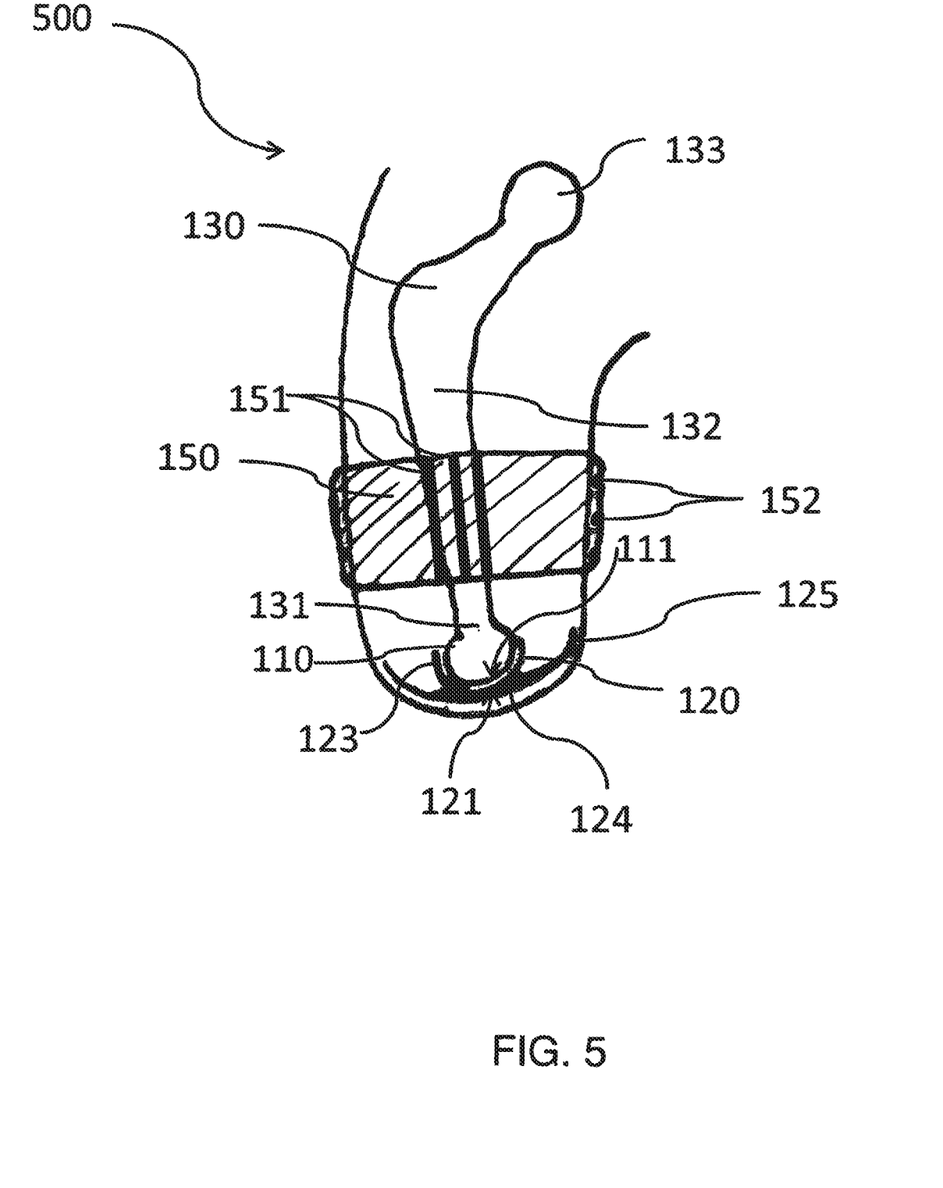
FIG. 5 shows another embodiment of a femur prosthesis system.

FIG. 5 shows an upper leg stump having a prosthesis system 500, wherein the sliding face 121 has an annular projection 123 as an articular socket edge. This projection 123 can be constructed in such a manner that the articular socket of the second joint member 120 and the joint ball of the first joint member 110 form a releasable plug type connection. To this end, the projection 123 is preferably constructed in a flexible manner and/or with resilient means. After the joint ball has been snap-fitted in the articular socket, the movability of the second joint member is not limited.

FIG. 5 further shows a peripheral band 150 for fixing a shaft (not shown). The band can be constructed from skin-compatible materials, such as fabric, silicone or other suitable materials. Preferably, there are used materials which adhere to the skin in order to improve the retention. The band 150 can be tightened similarly to a bandage in order to connect a shaft to the stump in a manner which is as stable as possible.

The band further has retention projections 151 and retention recesses 152 as retention means in order to be releasably connectable to the frame construction of a shaft. There can be used as retention means conventional forms which can be brought into engagement with a corresponding counter-form in the shaft (for example, teeth, grooves). The band and the retention means are used, in engagement with the corresponding retention devices on the shaft, to produce a rotation stability of the tightened shaft.

Figure 6:
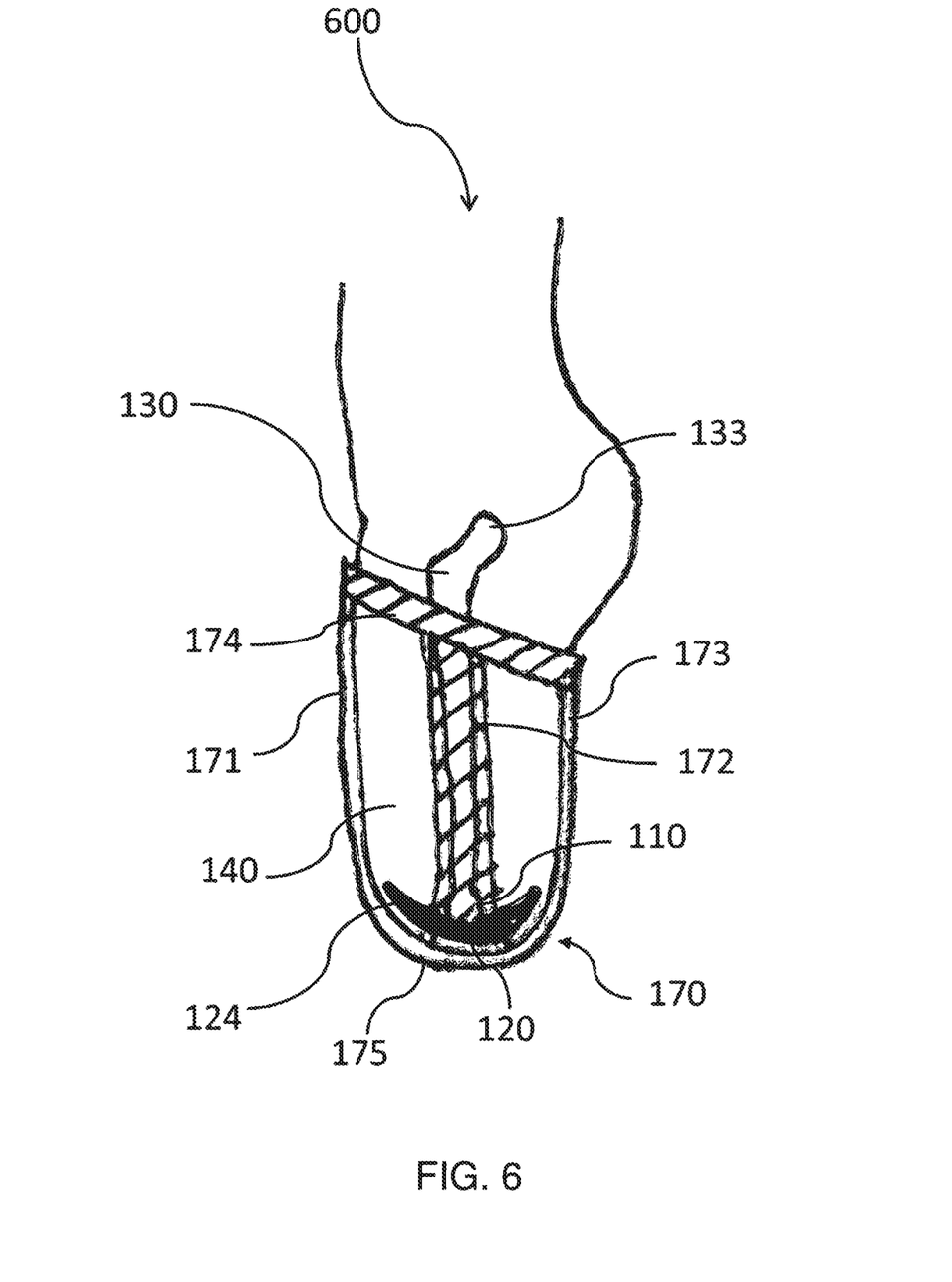
FIG. 6 shows another embodiment of a femur prosthesis system comprising a shaft.

FIG. 6 shows a frame shaft 170 for a femur prosthesis system 600. The circular band 150 shown in FIG. 5 is not shown for greater clarity of the shaft prosthesis system. The band 150 can, for example, be fixed to the retention means 152 shown in FIG. 6 on the arm 172 of the frame shaft 170. Additional arms 171 and 172 can be used to fix the shaft 170 to the band 150 (not shown) in a stable manner. Furthermore, a peripheral shaft edge 174 which can be constructed to be rigid, flexible or also partially flexible is provided for proximally fixing the frame shaft 170.

The open shaft concept with a frame construction and individual arms 171, 172 and 173 allows an exchange of air and temperature with the natural environment. This increases the wearing comfort for the user in comparison with shaft systems which are largely or completely closed. The open shaft does not limit the user in terms of his movement either as a result of material or cutting unlike conventional closed shaft systems.

A counter-plate 175 which is adapted to the outer form of the second joint member 120 is arranged in the lower region of the frame shaft. The counter-plate 175 allows a precisely fitting shaft. An optimum retention can thereby be achieved, wherein the risks of pressure sores and wound locations are reduced. This is particularly significant for the care of diabetes patients who require amputations. Furthermore, the prosthesis system can also be used in the case of bone cancer patients if a portion of a bone has to be removed. A loss of comfort as a result of a scoliotic pelvis or wear of clothing by an increased structural complexity can be generally prevented by means of the distal load transmission via the counter-plate 175 for prosthesis users.

Figure 7:
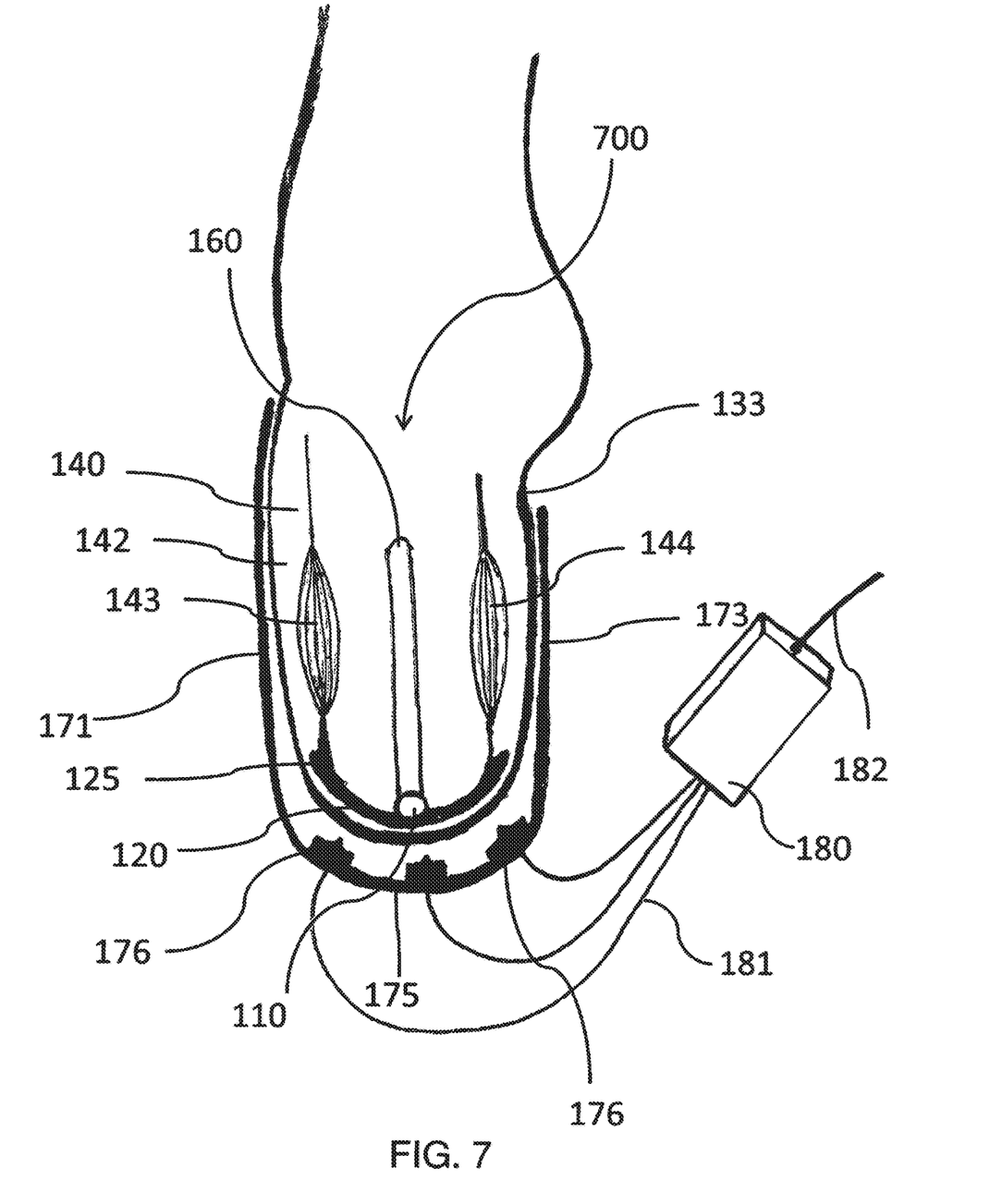
FIG. 7 is a cross-section of another embodiment of a femur prosthesis system comprising a shaft having an external measurement system with sensors for detecting the position and loading the subcutaneous joint member of the implant.

FIG. 7 shows another embodiment of the femur prosthesis system 700, wherein the system 700 is shown as a cross-section from the side. The section is shown by a medullary pin 160 which is anchored in a femur bone shaft and/or in a hip endoprosthesis (not shown).

In the sectional view shown, muscles which are relevant for controlling the movements of an extracorporeal prosthesis (not shown) are schematically shown. Stretching muscles 143 are located at the front side of the upper leg 142 while bending muscles 144 are schematically shown at the rear side of the lower leg. These muscle groups 143 and 144 can be fixed by means of suitable retention devices or by means of holes to the radial edge region 125 of the second joint member 120. The muscles 143, 144 can be sewn, for example, to the lower side of the radial edge region 125. To this end, holes can be formed in the radial edge region 125. Depending on the muscle position, a suitable hole for connection can be selected in order to receive a muscular attachment. Alternatively or additionally to sewing, the musculature can also grow on surfaces suitable therefor or fuse with a suitable material.

The muscles can deliberately be tensioned by the prosthesis user so that an inclination of the second joint member 120 is brought about. This inclination can be detected by the measurement sensors 176. If the end plate 124 tilts, for example, by tensioning the rear muscle 144 upwards at the rear and downwards at the front, pressure is applied to the front pressure sensor 176. In this manner, the position of the second joint member 120 can be established. The detected measurement signals are forwarded via connection lines which are preferably integrated in the shaft to a control unit 180. In this manner, a bending of the knee of an extracorporeal leg prosthesis can be controlled.

The control unit 180 has at least one microprocessor and a transmission unit 182. Alternatively to a transmission unit, the signal for control can be transmitted to the control unit via a cable connection or other suitable means. The components shown are not illustrated so as to be true to scale by way of illustration and are dimensioned for use so that they can be integrated in the shaft or the exoprosthesis. On the basis of the measurement data detected, control signals can be transmitted to components of an extracorporeal prosthesis. The transmission of the measurement data can also be brought about wirelessly via conventional transmission and receiving devices instead of via signal lines 181. Conventional actuators such as valves or motors can be used for moving the controlled extracorporeal prosthesis elements.

Figure 8:
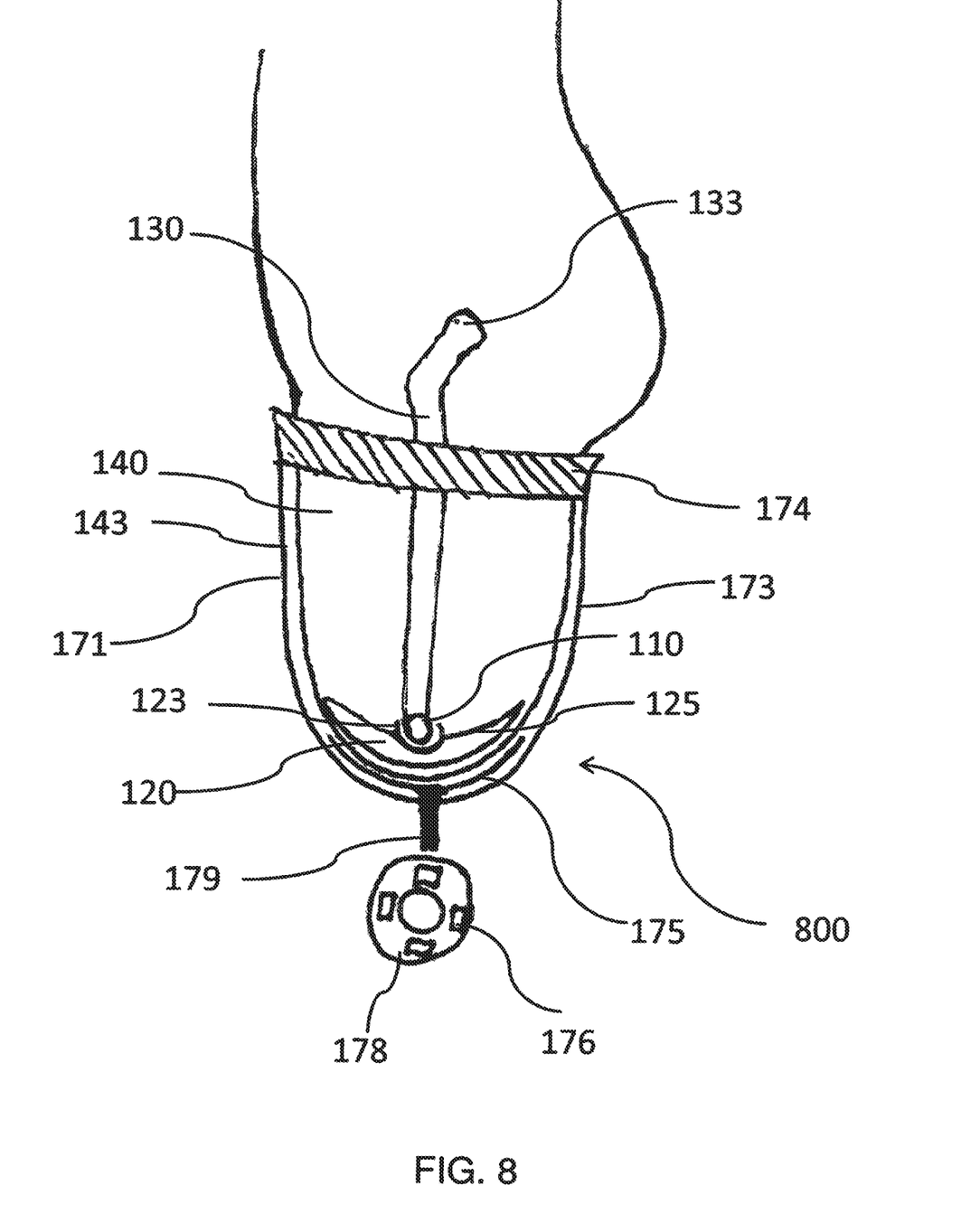
FIG. 8 is a cross-section of another embodiment of a prosthesis system having another external measurement system which is fitted under the shaft.

FIG. 8 is a lateral cross-section of an additional embodiment of a prosthesis system 800 with a frame shaft 170 together with a plan view of an external measurement system which is fitted under the shaft. The measurement system is constructed in the form of a pipe element 178, wherein the pipe element 178 can receive a pin 179 which is connected to the counter-plate 175. The movement of the counter-plate 175 located in the shaft between the stump and frame can be measured by means of suitable sensors 176. As illustrated in the schematic plan view in FIG. 8, the pipe element 178 may have a plurality of measurement sensors 176.

This measurement system constitutes an alternative or additional measurement method for the movements of the end plate 124. In this case, the movement of the end plate 124 is transmitted to the counter-plate 175 which acts as an intermediate plate. The external measurement system can thereby measure the movement of a movable portion in the shaft—in this case, the counter-plate 175—and/or the loading of the prosthesis.

FIG. 8 shows a femur prosthesis system, wherein the position of the shaft edge 174 which extends round the upper thigh is schematically indicated. The femur bone 130 with the femur head 133 is located in the soft part mantle 140 of the upper leg.

The first joint member 110 is located as the articular head in the articular socket of the second joint member 120. The articular socket is delimited by the annular projection 123. Furthermore, the second joint member 120 has a radially peripheral edge region 125. The counter-plate 175 is adapted to the outer form of the subcutaneous second joint member 120.

Figure 9:
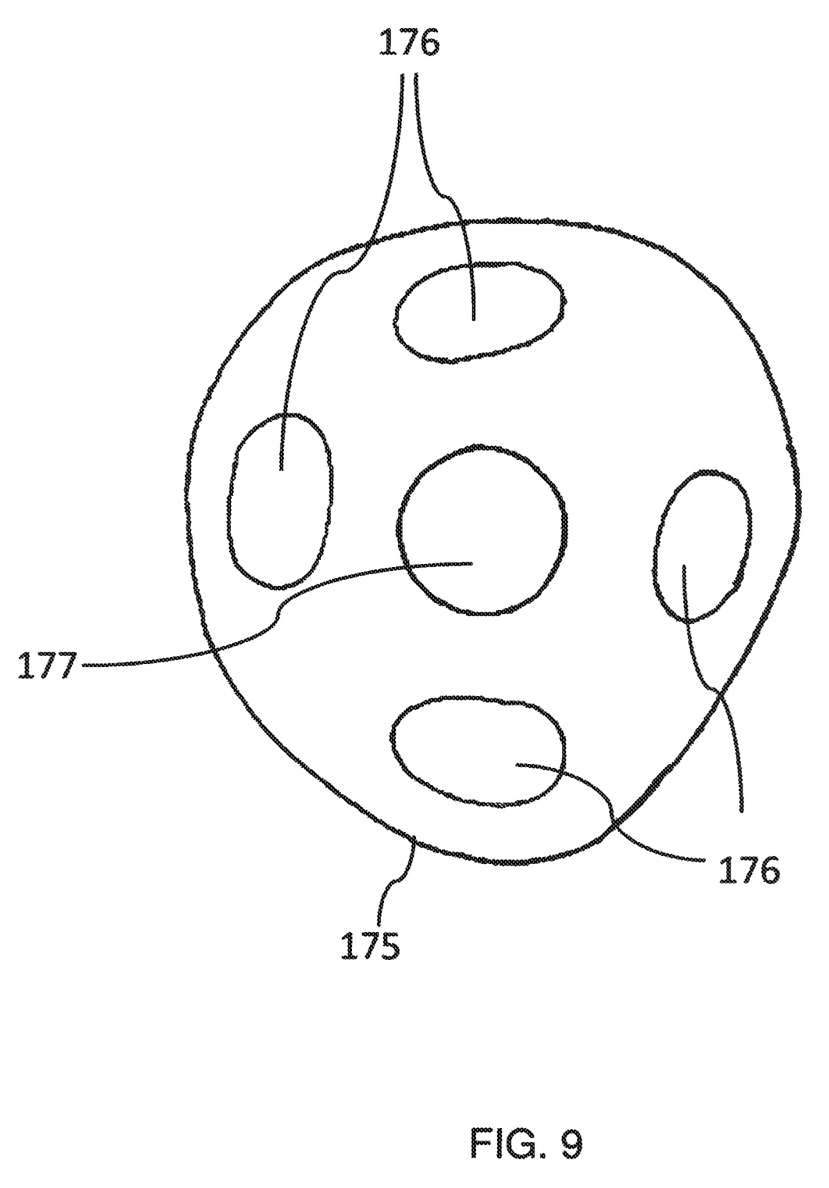
FIG. 9 is a schematic plan view of an external measurement system in the form of a counter-plate.

FIG. 9 is a detailed view of an external measurement system in the form of a counter-plate 175 (cf. FIG. 7). Pressure sensors are arranged in the radial edge region of the counter-plate 175 in order to be able to detect the position or positional changes of the second joint member 120. Axial forces can be measured at the centre 177. Where applicable, an exoprosthesis can be connected via the centre 177 of the counter-plate (cf. pin 179 in FIG. 8) and where applicable signal lines can be directed to controllable components.

The invention is not limited to the embodiments shown but can instead also be used for other amputated or exarticulated limbs.

LIST OF REFERENCE NUMERALS

100 Prosthesis system
101 Implant
110 First joint member
111 Sliding face of first joint member
120 Second joint member
121 Sliding face of second joint member
122 Outer face of end portion
123 Annular projection
124 End portion of second joint member
125 Radially peripheral edge region
130 Femur bone
131 Distal shaft end
132 Bone shaft
133 Femur head
134 Knee-cap
135 Tibia
136 Fibula
137 Distal fibula shaft end
140 Soft part mantle
141 Distal amputation stump end
142 Upper leg
143 Stretching muscles
144 Bending muscles
150 Peripheral band
151 Retention projections
152 Retention recesses
160 Medullary pin
161 Distal medullary pin end
162 Proximal medullary pin end 170 Frame shaft
171 Arm of frame shaft
172 Additional arm of frame shaft
173 Additional arm
174 Peripheral shaft edge
175 Counter-plate
176 Measurement sensors
177 Centre of counter-plate
178 Pipe element
179 Pin
180 Control unit
181 Signal line
182 Transmission unit
200 Prosthesis system with medullary pin
300 Femur prosthesis system
400 Tibia prosthesis system
500 Band for a femur prosthesis system
600 Prosthesis system with shaft
700 Additional prosthesis system with shaft
800 Additional prosthesis system with shaft

The invention claimed is:

1. A prosthesis system for human limbs, the prosthesis system comprising:
   an intracorporeal implant having at least two mutually movable joint members that make up a joint;
   wherein the first joint member can be connected to a bone portion;
   wherein the second joint member is not connected to a bone portion and has an end portion configured to be arranged subcutaneously at a side thereof remote from the joint; and
   wherein the end portion is constructed in a plate-like manner.

2. The prosthesis system according to claim 1, wherein the end portion has a convex-curved outer face.

3. The prosthesis system according to claim 1, wherein the first joint member is in the form of an articular head and the second joint member is in the form of an articular socket.

4. The prosthesis system according to claim 1, wherein the first joint member is constructed in a hollow manner and has fixing means for connection to the bone portion which are selected from the group consisting of bone-forming material, bone cement and adhesive.

5. The prosthesis system according claim 1, wherein the first joint member can be connected to a bone portion via a medullary pin and/or a screw unit.

6. The prosthesis system according to claim 1, wherein the end portion has a radially peripheral edge region.

7. The prosthesis system according claim 1, wherein the end portion of the second joint member has faces and/or material for connecting muscles.

8. The prosthesis system according to claim 1, further having a shaft configured to at least partially surround a limb stump of a prosthesis user in order to be connected to extracorporeal prosthesis mechanisms.

9. The prosthesis system according to claim 8, wherein the shaft has a counter-plate, the form of which is adapted to an outer form of the second joint member.

10. The prosthesis system according to claim 8, wherein the shaft is in the form of a frame shaft.

11. The prosthesis system according to claim 8, wherein the shaft has a band extending in a circular manner as a retention device for the shaft.

12. The prosthesis system according to claim 1, wherein there is provided at least one measurement system configured to be external to a human limb and comprising measurement sensors for detecting a position of the second joint member.

13. The prosthesis system according to claim 12, wherein the at least one external measurement system is constructed as a counter-plate.

14. The prosthesis system according to claim 12, further having a control unit, wherein extracorporeal prosthesis mechanisms can be controlled responsive to measurement signals detected by the at least one measurement system.

15. The prosthesis system according to claim 1, wherein there is provided at least one measurement system configured to be internal to a human limb in order to detect at least one of a position and a loading of at least the second joint member.

* * * * *